United States Patent [19]

Levy et al.

[11] Patent Number: 4,472,357

[45] Date of Patent: Sep. 18, 1984

[54] BLOOD BANK CUVETTE CASSETTE AND LABEL THEREFOR

[75] Inventors: Didya D. Levy, Brooklyn; Richard E. Scordato, Scarsdale, both of N.Y.

[73] Assignee: Medical Laboratory Automation, Inc., Mount Vernon, N.Y.

[21] Appl. No.: 322,639

[22] Filed: Nov. 18, 1981

[51] Int. Cl.³ .......................................... B01L 14/00
[52] U.S. Cl. .................................... 422/102; 40/312; 128/762; 128/771; 206/459; 206/820; 220/23.4; 604/403; 604/404
[58] Field of Search .................. 422/58, 102; 356/246; 206/443, 459, 524.3, 524.4, 820; 428/35; 128/763, 764, 765, 272, 762, 771; 40/2 R, 312; 220/23.4; 604/403, 404

[56] References Cited

U.S. PATENT DOCUMENTS

| | | | |
|---|---|---|---|
| 3,097,070 | 7/1963 | Aldrich et al. | 422/102 |
| 3,219,421 | 11/1965 | Schwarz, Jr. et al. | 422/102 |
| 3,432,275 | 3/1969 | Unger | 422/102 |
| 3,715,856 | 2/1973 | Borel | 206/820 X |
| 3,759,374 | 9/1973 | Helger et al. | 356/246 X |
| 3,773,250 | 11/1973 | Phillips | 40/2 R X |
| 3,905,772 | 9/1975 | Martnett et al. | 422/72 |
| 3,907,505 | 9/1975 | Beall et al. | 422/102 |
| 3,917,120 | 11/1975 | Larenz et al. | 206/820 X |
| 3,941,858 | 3/1976 | Shepherd et al. | 264/183 X |
| 4,122,947 | 10/1978 | Falla | 40/2 R X |
| 4,128,954 | 12/1978 | White | 40/2 R X |
| 4,154,795 | 5/1979 | Thorne | 422/102 X |
| 4,226,503 | 10/1980 | Irazoqui et al. | 356/246 X |
| 4,311,250 | 1/1982 | Ravve et al. | 428/35 X |

FOREIGN PATENT DOCUMENTS

| | | | |
|---|---|---|---|
| 578807 | 6/1933 | Fed. Rep. of Germany | 422/102 |
| 2435317 | 2/1976 | Fed. Rep. of Germany | 356/246 |

Primary Examiner—Arnold Turk
Attorney, Agent, or Firm—William P. Keegan

[57] ABSTRACT

A plurality of cuvettes joined together by breakable links between each cuvette for use in testing blood for its ABO classification and the presence of a typical antibodies, and for crossmatching blood for compatibility, together with label means for indicating the reagents used in each cuvette and the identity of the person whose blood is being tested. The cuvettes may be adapted to accept a closure means which permits the cuvettes to be pre-packaged with reagents required to carry out blood tests. The cuvettes have a hydrophilic polymer coating thereon that is non-destructive of red blood cells.

7 Claims, 11 Drawing Figures

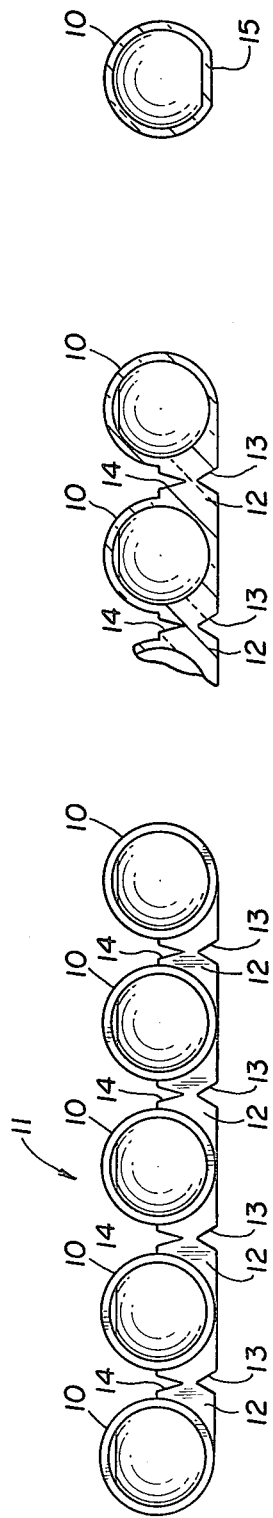

BLOOD BANK CUVETTE CASSETTE AND LABEL THEREFOR

FIELD OF THE INVENTION

This invention relates to cuvettes used in a blood processing center for typing blood according to the ABO classification system, for screening the blood to identify atypical antibodies, and for crossmatching the blood for compatibility with that of potential donors. The invention also relates to an indicia means for positively identifying the cuvettes both as to the reagents used therein for carrying out the aforesaid procedures and the person whose blood is being classified.

BACKGROUND OF THE INVENTION

The importance of error free classification of a patient's blood and a donor's blood when the latter is to be transfused to the patient is so well understood by those working in the field of blood banking that it need not be reiterated here other than to say that transfusion of incompatible blood to a patient can lead to severe hemolytic reactions and even to the death of the patient. This incompatibility arises from the fact that red blood cells vary in their structure by what are called antigens so that one person's blood cells may have certain antigens that differ from those carried by the red blood cells of another person. If foreign antigens are introduced into a person's blood stream, his immunological system immediately produces antibodies that destroy the foreign material, i.e., the introduced blood cells carrying the foreign antigen. The incompatibility may also arise from the donor's serum which may contain antibodies that would destroy the patient's red blood cells because of the antigens carried thereon. Therefore, every effort must be made to facilitate the proper classification of blood and to properly and positively identify the classified blood so that incompatible blood transfusions are avoided.

The principal blood cell antigens are designated A and B, with some cells having A antigens, some having B antigens, some having both A and B antigens, and some having neither A nor B antigens. Thus, blood having red cells carrying A antigens is referred to as Type A blood, that having cells carrying B antigens as Type B blood, that having cells carrying both A and B antigens as Type AB blood, and that having cells which do not carry either antigen as Type O blood. Other antigens are important, such as the D and other Rh antigens. The ABO blood group is generally determined by a forward typing protocol in which a person's red cells are mixed with antiserum reagents containing known antibodies to see if agglutination takes place. Thus, red cells are mixed with anti-A serum, anti-B serum, anti-AB serum, and anti-D serum. If the mixture of anti-A serum and the patient's red cells agglutinate and the mixture of anti-B serum and red cells does not, the patient's blood group is Type A. That is, the patient's red cells carry the A antigen. If the reverse result obtains, then the patient's blood group is Type B. In both of these instances, the anti-AB mixture would agglutinate. If agglutination occurs in both mixtures, and in the anti-AB mixture, the blood group is Type AB, and if agglutination is absent in all mixtures, the blood group is Type O. If the D antigen is present, i.e., the anti-D serum-cell mixture agglutinates, the blood group is positive, e.g., Type A+, and if the D antigen is absent (when the mixture does not agglutinate) the blood group is negative, e.g., Type B—.

It is so important to make a correct determination of a person's blood type when a blood transfusion is contemplated, or may become necessary, that a double check called reverse typing is ordinarily made in the typing procedure. Thus, in addition to observing if there is an agglutination reaction when the person's red cells are mixed with antibody reagents such as anti-A serum, the person's serum is mixed with standard red cell reagents having A antigens and B antigens. If the serum tests positively, i.e., agglutinates, with the A antigen red cells and negatively with the B antigen red cells, then the person's blood group is Type B. If the reverse result is observed, then the person's blood group is Type A, and if the results of both tests are negative, the blood group is Type AB. If both tests are positive, the blood group is Type O.

In general, the foregoing blood groups offer a satisfactory preliminary categorization of blood types, but there are other factors, i.e., other antigens, which are atypical and have to be taken into account to assure, essentially, absolute compatibility between a patient's blood and that of a donor which is to be transfused to the patient. Therefore, still other tests are conducted to determine whether or not a person's serum contains antibodies that would destroy red cells that carry antigens that are less frequently encountered but which may be carried by a donor's red cells. In carrying out these other tests, a person's serum is mixed with reagent red cells to determine whether or not agglutination occurs. There may, in fact, be several different reagent red cells, such comprising red cells carrying different groups of antigens. If none of the serum reagent red cells mixtures agglutinate, there is essentially no incompatibility between the person's serum and any of the antigens carried by the reagent blood cells. In other words, the person's serum contains no antibodies that would destroy red cells carrying antigens of the type carried by the reagent red cells. If, on the other hand, agglutination occurs in a serum reagent red cell mixture, still other tests must be performed to determine the particular antibody causing the agglutination. Even after the tests for atypical antibodies are completed and a complete profile of a patient's blood is known, and a tentative assignment of donors' blood (which had undergone the same battery of tests and has a profile similar to that of the patient's blood) is made for the patient, still other tests are performed to determine if the patient's serum agglutinates red cells of the various tentative donors. This other testing is referred to as crossmatching, and only if there is no agglutination will a donor's blood be suitable for transfusion to the patient.

It is clear from the foregoing that many separate tests, each using a separate reaction vessel or cuvette, are performed using a person's red cells and serum and that the results of those tests must be recorded and tabulated with great precision to assure the proper classification of a blood type and the association of that data with a particular person. Thus, each individual cuvette must be marked to identify the person whose blood is being tested and the reagent that is added to the cuvette so that each separate test result can be recorded for the person. In this connection, it is noted that clerical mistakes are generally conceded to be the single largest cause of errors in a blood bank. Transcription and filing errors account for more than 93% of all blood bank errors. See H. F. Taswell and C. L. Sonnenberg, "Blood Bank Errors: A New Functional Classification", Abstracts, American Association of Blood Banks, 1979, page 24.

While the prior art has addressed this problem, see particularly U.S. Pat. No. 3,033,412 which discloses clip means for joining a number of test tubes together, and U.S. Pat. No. 3,905,772 which discloses a unitary group of cuvettes and an indicia member which facilitates forward and reverse typing of blood groups according to the general ABO classifications, it has been found that blood banks, in general, still adhere to their old methods of using individual test tubes or cuvettes which are individually marked with a marking pen to identify the red cell reagent test or serum reagent test that occurs in each cuvette. The cuvettes are also individually marked to identify the donor of the red cells and serum, that is, the person whose blood is being typed and classified.

GENERAL DESCRIPTION OF THE INVENTION

The object of the present invention is to provide an improved system for typing blood according to the ABO classification system.

Another object of the invention is to positively associate each test with a blood donor.

Still another object of the invention is to facilitate the performance of blood tests other than the forward and reverse typing tests.

Yet another object of the invention is to provide an improved cuvette article and cuvette marking means for use in performing blood bank tests.

In carrying out the invention, a plurality of cuvettes are provided in a linear configuration which is adapted to accommodate a label that carries a common mark for each cuvette and an individual mark peculiar to each cuvette. The common mark serves to identify the source, i.e., the donor, of the blood component added to each cuvette and the individual mark serves to identify the blood component and the reagent to be mixed in the cuvette. In a preferred embodiment, the cuvettes are molded of a suitable plastic and the connecting piece joining each cuvette to the adjoining cuvette is breakable so that one or more cuvettes may be separated from the others. Moreover, the interiors of the cuvettes will have a wettability equivalent to that of glass test tubes. In a further embodiment of the invention, the reagents required for performing the agglutination tests are placed in the cuvettes which are then sealed and labeled so that it is only necessary for a laboratory technician to unseal the cuvettes and add the appropriate blood component prior to performing the testing protocol.

Features and advantages of the invention may be gained from the foregoing and from the description of a preferred embodiment thereof which follows.

DESCRIPTION OF THE DRAWING

FIG. 2 is a top plan view of the group of cuvettes;

FIG. 4 is a sectional view taken on line 4—4 of FIG. 1;

FIG. 6 is a sectional view taken on line 6—6 of FIG. 5;

FIG. 7 is an illustrative view of a typical label used in conjunction with the group of cuvettes shown in FIG. 1;

DETAILED DESCRIPTION OF THE INVENTION

Figure 1:
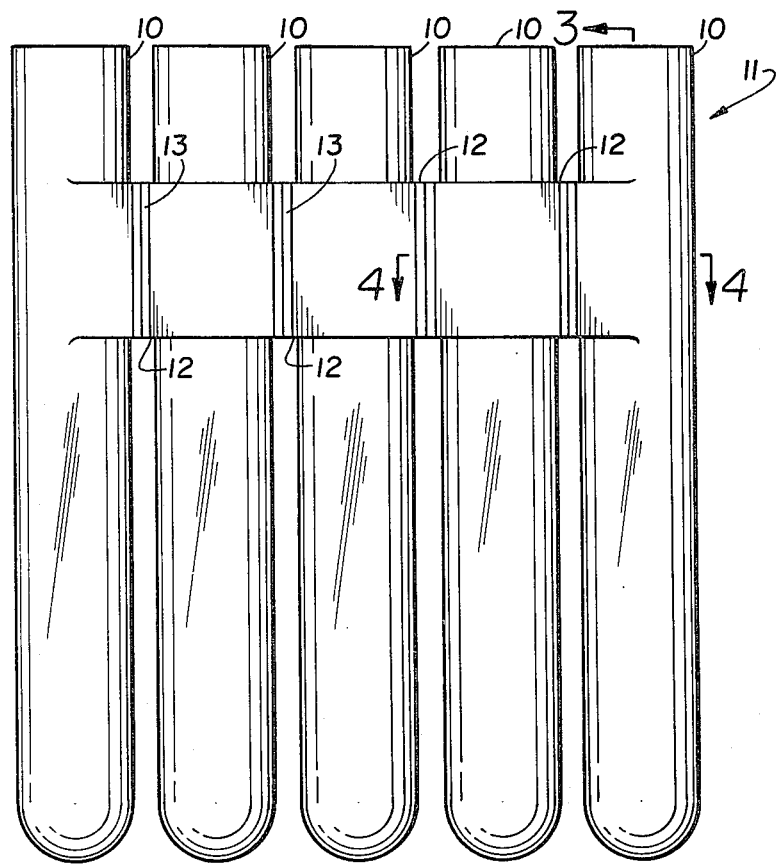
FIG. 1 is a front elevational view of a group of cuvettes provided in accordance with the present invention.

Referring to the drawing, a linear array of five individual cuvettes 10 are illustrated as one integral unit or cassette 11 of cuvettes. More or fewer individual cuvettes could be provided in a cassette. The cassette 11 is preferably molded in one piece from a general purpose clear polystyrene with the connecting bridges 12 notched as shown at 13 and 14. While other plastics can be used, polystyrene is preferred since it is inexpensive, injection moldable, colorless, and relatively inflexible. The notches 13 and 14 permit the bridge between two cuvettes 10 to be broken by the application of a small flexing force to the weakened, i.e., notched, part of the bridge 12. The front surface of the connecting bridges, except for the front notches 13, form a flat surface in front of each cuvette. These flat surfaces will accommodate a label and hold it in a readily readable position as hereinafter described.

As noted, cuvette cassette 11 is preferably molded from a polystyrene resin, but such a cassette would generally be unsatisfactory for blood bank use. The reason for this is that the cuvettes would be hydrophobic, a property that prevents fluids from readily flowing in the cuvettes. Such hydrophobicity would cause saline suspensions of cells to bead up within the cuvette and make examination of its contents for agglutination nearly impossible. Thus, if polystyrene is to be used to mold the cuvettes, it becomes desirable to make at least the interiors of the cuvettes wettable. This can be done by coating the inside of the cuvettes with a hydrophilic polymer. However, all such coatings will not be suitable for cuvettes used in a blood bank because some such coatings will lyse cells or potentiate reactions that cause cells to agglutinate and thereby give false positive results. Moreover, even a plastic that is itself wettable may not be suitable because it will lyse cells or potentiate reactions.

The following material has been found satisfactory for coating polystyrene cuvettes for blood bank usage. That is, it will make the polystyrene wettable and it will not lyse red cells. A diluent composed of 95% isopropanol and 5% water on a volume basis is added to a monomer comprising optical grade 2-hydroxyethyl methacrylate (available from Polysciences, Inc., Warren, Pa. on a monomer to diluent weight ratio of 20:80. A redox catalyst of sodium metabisulfite and ammonium persulfate in a 1:1 weight ratio is then added to the deoxygenated monomer mixture in a 1:100 (redox:monomer) weight ratio. The resulting solution is then stirred vigorously for two to six hours under a nitrogen blanket, after which it may be stored away from light and heat. This 20% polymer formulation is further diluted in neat isopropanol to a solids content of about $\frac{3}{4}$% to 1% by weight to obtain the final coating solution. An adequate coating may be obtained by swabbing the lumen of a cuvette with a cotton tipped applicator saturated with the coating solution and then drying the cuvette in an inverted position while blowing a stream of air at about 15 p.s.i. into the lumen for ten to fifteen seconds. While the coating will not erode when subjected to normal blood bank usage, it is soluble in alcohol and contact with solutions containing alcohol should be avoided.

Other wetting agents may be used to coat cuvettes, but the described polymer and coating procedure are preferred. Alternatively, a suitable wetting agent may be added to the bulk resin from which the cuvettes are molded. Or, glass test tubes could be held in a collar member that is breakable to allow one or more of the test tubes to be separated from the remaining test tubes in the cassette.

Figure 3:
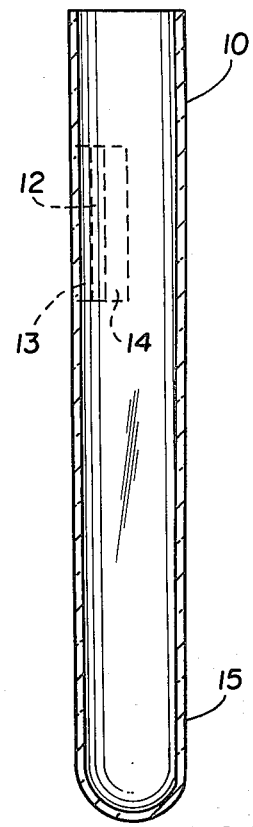
FIG. 3 is a side elevational view of the group of cuvettes.
Figure 5:
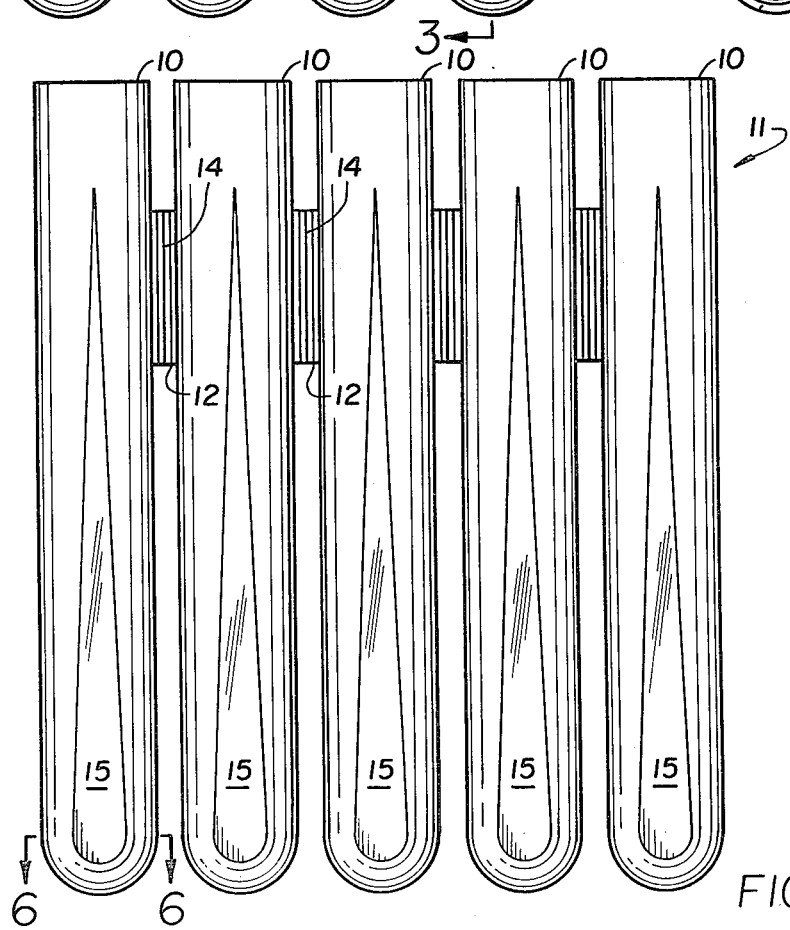
FIG. 5 is a fragmentary rear elevational view of the group of cuvettes.

Referring again to the drawing, and particularly to FIGS. 3 and 5, it will be noted that the rear surface of each cuvette is formed with a tear-shaped flat 15 which enhances observation of reactions in the cuvettes. The bottom portion of tear-shaped flat 15, i.e., the widest part of the flat near the base of the cuvette, forces a cell suspension (which typically may be about 150 microliters in volume) to thin out into a monolayer of cells thereby permitting the observer an unobstructed view of the cell suspension. For observation, a microscope reader of the type disclosed in U.S. Pat. No. 4,226,503 may be used. The apex of flat 15 near the top of the cuvette compels all cells, agglutinated and non-agglutinated, to flow past a single point thereby affording examination of the entire contents of the cuvette.

FIG. 7 illustrates a sticky back label 20 having a format that is particularly suited for use with the cuvette cassette 11 of FIG. 1 when the latter is employed in standard blood typing tests. Each label comprises a plurality of patient identification stickers 21, each patient being assigned an accession number which is the same as the number printed on the stickers. Each sticker may be peeled off the backing sheet for application to blood specimen tubes, request slips, work sheets, log book records, donor file cards, and the like. In short, the numbered stickers 21 can be applied to any item that has to be associated with the patient to whom the sticker number has been assigned.

Label 20 further includes a first cassette sticker 22, a second cassette sticker 23, and a third cassette sticker 24. These stickers are also peel-off stickers and may be applied to the front of a cuvette cassette 11 along the flat surfaces of bridges 12. It should be noted that the solid lines 25 separating stickers 21 from each other, and stickers 22, 23, and 24 from each other and from stickers 21, represent slits that completely separate the stickers and permit them to be individually peeled from the label backing sheet (not shown). Each of stickers 22, 23, and 24 may be peeled from the backing sheet as a unit. The dotted lines 26 separating the marks printed on stickers 22, 23, and 24 represent perforations which permit the stickers to be separated when a tearing force is applied to the perforations. The particular marks printed on the stickers 22, 23, and 24 will be described when the use of the stickers and cassettes 11 is hereinafter described. It will be noted at this time, however, that each indicia portion of stickers 22, 23, and 24 also bears the accession number that identifies a patient. Thus, whenever the sticker is applied to a cassette 11, each cuvette of the cassette will be marked with an accession or patient identification number.

Figure 8:
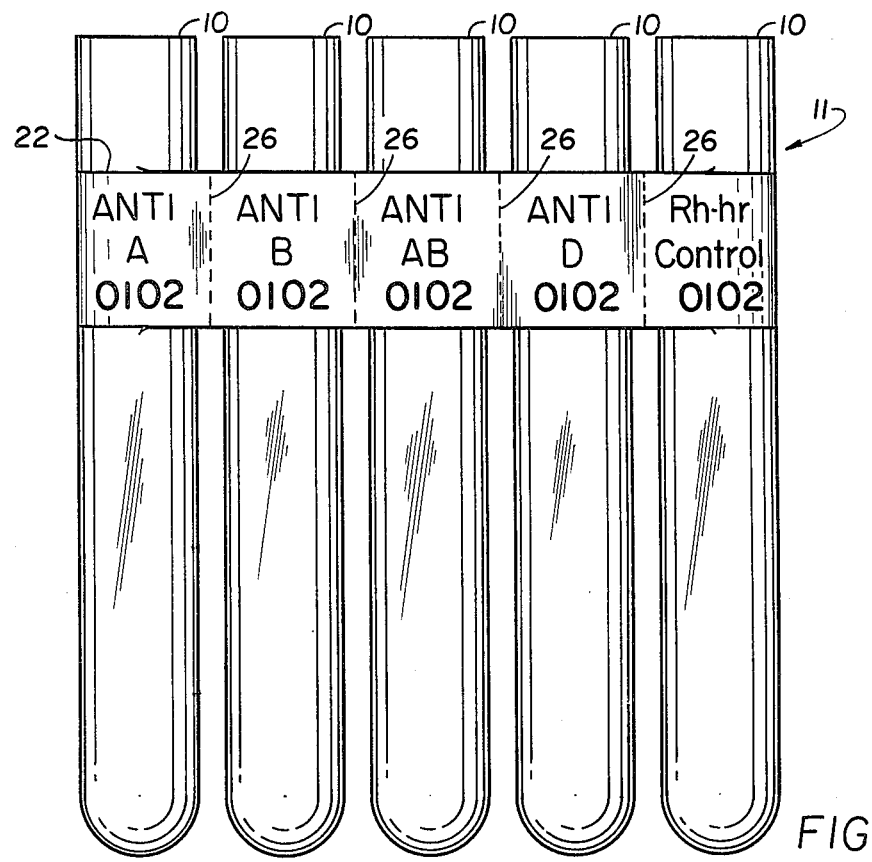
FIG. 8 is a fragmentary front elevational view showing the group of cuvettes after they are labeled.

Cassettes 11 and labels 20 may be incorporated into the blood processing system of a blood bank in the following fashion. Assume that a sample of a patient's blood arrives at the blood bank in a sample tube together with a form requesting classification of the blood sample. This might be done in preparation for a blood transfusion that may become necessary or had already been prescribed. Not only would the patient's blood have to be tested, but suitable donor blood would also have to be identified. The receiving desk would assign an accession number to the patient (this would be the number on the next available label 20). The patient's name and the accession number are entered in a log book. A sticker bearing the accession number would be peeled from label 20 and applied to the blood sample tube. A sticker is also applied to the request form. The thus marked sample tube and request form together with the rest of label 20 bearing the accession number on stickers 21, 22, 23, and 24 would be delivered to the technician who is to do the blood typing. The technician first separates the blood sample into its component red cells and serum and suitably marks the tubes containing the same with stickers 21. Then stickers 22, 23, and 24 are affixed to three cassettes 11. See, for example, FIG. 8.

The cassette with sticker 22 applied thereto is used in the forward typing protocol. Sticker 22 bears the marks anti A, anti B, anti AB, anti D, and Rh-hr Control, and each mark, in effect, is applied to an individual cuvette 10 of the cassette. The accession number assigned to the patient also is printed in association with the aforesaid marks and it too is similarly applied to each individual cuvette. A volume of the patient's red cells is placed in each cuvette. A different reagent, as indicated by the marks on sticker 22, is added to each cuvette along with the patient's red cells. The mixtures are spun in a centrifuge and observed macroscopically for agglutinations. The Rh-hr Control reagent acts as a control and it should always give a negative reaction, i.e., no agglutination, when mixed with the patient's red cells. If the Rh-hr Control mixture agglutinates (in which case the anti D mixture will also have agglutinated), it is an indication that the anti D mixture may have agglutinated for anomalous reasons, in which case the tests should be rerun with new or fresh anti D reagent. The agglutination results are entered on a work sheet along with an accession number sticker 21.

Depending on which mixtures agglutinate, the blood group of the red cells is determined. Thus, if the anti A mixture agglutinates and the anti B mixture does not, the blood group is Type A. If the reverse result obtains, the blood group is Type B. If agglutination occurs in both mixtures, the blood group is Type AB, and if no agglutination occurs in any of the anti A, anti B, and anti AB mixtures, the blood group is Type O. If the anti D mixture agglutinates then the group is positive, e.g., Type A+, and if it does not the group is negative. However, if the anti D mixture does not agglutinate, a further test is performed to verify the negative result.

In carrying out this further test, the anti D reagent mixture which tested negative and the Rh-hr Control mixture, or more precisely, the cuvettes containing the mixtures are preferably broken away from the other three cuvettes in the cassette. The latter three cuvettes may be discarded since their test results have been recorded. The separation of the cassette into two parts is accomplished by grasping the anti AB cuvette and the anti D cuvette and bending the cassette 11 until it breaks at the notched bridge between the two cuvettes. The perforations between the anti AB and anti D marks on sticker 22 permits the sticker to tear apart so that the two parts of the cassette remain properly labeled.

Albumin or another potentiating medium is added to the anti D and the Rh-hr Control cuvettes and the mixtures incubated at 37 degrees C. for fifteen to thirty minutes. The mixtures are then washed in a cell washer and the supernatent decanted so that only red cells remain in each cuvette. To the washed cells is added anti human globulin or Coombs serum, the mixtures centrifuged and observed for agglutinations. If the anti D mixture agglutinates, then the blood group is positive; weakly positive, but positive. If the anti D mixture does not agglutinate, the blood group is in fact negative. In this case, the negative result of the initial anti D reaction is confirmed. In all events, the Rh-hr Control mixture should not agglutinate. If it does, it is an indication of some anomaly that requires the tests to be rerun.

The technician then turns to the second cassette labeled with sticker 23. Here the sticker marks, reading from left to right, are A Cell, B Cell, Screen 1, Screen 2, and Auto Control. The A Cell and the B Cell cuvettes are used to reverse type the patient's blood and confirm the results of the forward typing. The cuvettes labeled Screen 1 and Screen 2 are used to initially test for the presence of atypical antibodies in the patient's serum which would destroy red cells that carry less common antigens if the latter is transfused to the patient. A volume of the patient's serum is placed in each of the cuvettes of the second cassette that has been marked with sticker 23. To the first cuvette is added a reagent of standard red cells carrying the A antigen, to the second a reagent in which the red cells carry the B antigen. Considering these two cuvettes alone for the present, the mixtures are centrifuged and observed for agglutinations. If the A cell mixture agglutinates and the B cell mixture does not, then the blood group is Type B. If the reverse result is observed, the blood group is Type A, and if both tests are negative, i.e., neither agglutinates, the blood group is Type AB. If both tests are positive, the blood group is Type O. The reverse typing tests are used to double check or confirm the forward typing results.

The patient's red cells are added to the patient's serum in the cuvette marked Auto Control, the mixture centrifuged and observed for agglutination. Of course, there whould be no agglutination. If there is an agglutination, it will alert the blood bank to the fact that the patient, most likely, is receiving some medication such, for example, as quinidine or high dosages of penicillin.

The reagents added to the Screen 1 and Screen 2 cuvettes are special reagent blood cells that carry a spectrum of atypical or relatively unusual antigens. The reagents may be those marketed by Ortho Diagnostics, Inc. of Raritan, N.J. under the trademark "Selectogen". The Screen 1 and Screen 2 mixtures, reagent plus patient's serum, are centrifuged and observed macroscopically for agglutinations. In general agglutinations will not be observed in the screen mixtures. It is to be understood that all of the cuvettes in the cassette will be observed at the same time for agglutinations in the mixtures therein. Thereafter, the two cuvettes containing the Screen 1 and Screen 2 mixtures are separated from the remaining cuvettes in the cassette so that these mixtures can be further processed. Since the protocol for further processing is the same as that to which the anti D and the Rh-hr Control mixtures are subjected when the anti D mixture initially reacts negatively, the Screen 1 and Screen 2 mixtures can be processed along with those other two mixtures. Considering only the Screen 1 and the Screen 2 mixtures, albumin or another potentiating medium is added to each mixture and both mixtures are incubated at 37 degrees C. for fifteen to thirty minutes. The cuvettes are then placed in a cell washer and the supernatent decanted to leave only the red cells in the cuvettes. Coombs serum is added to the red cells in each cuvette, the mixtures centrifuged and observed for agglutinations. If either or both mixtures agglutinate, then a further panel or panels of tests must be run to determine which specific atypical antibody or antibodies are present in the patient's serum. Each panel may contain as many as twelve different special reagent red cells which must be tested for agglutinations by mixing with the patient's serum. Since the agglutinations will be minimal, if they occur at all, the protocol for doing the panel testing involves the addition of albumin to the mixtures, incubation, cell washing, the addition of Coombs serum, centrifugation, and observation, all as previously described for other reagent mixtures. Reagents for the further test panels are marketed by Ortho Diagnostics, Inc. as Reagent Red Blood Cells Panel A and Panel B under the trademark "Resolve". If after the addition of Coombs serum the mixtures test negatively, then the patient's serum contains no atypical antibodies. To further confirm the negative result, the technician will add reagent check cells to the mixture which then should agglutinate. Such agglutination confirms the earlier negative reaction.

At this time, after running the screen tests, the patient's blood type will have been determined, and the presence or absence of all significant atypical antibodies in the patient's serum will also be known. To prepare for a transfusion, blood from several donors which has the same profile, i.e., blood group classification and atypical antibody characteristics (as determined by tests on the donors' blood identical to the tests described above for the patient), will be selected and tested for complete compatibility with the patient's blood. This further testing is referred to as crossmatching and is done in a third cassette 11 to which sticker 24 is applied. Thus, the blood from up to five donors can be crossmatched with the patient's blood. Or, four donor samples can be crossmatched with the fifth cuvette in the cassette being used as an auto control as previously described.

The donor cuvettes will each receive a volume of red cells from a different donor. To each cuvette is added the patient's serum. The mixtures are centrifuged and the reactions observed. If a mixture agglutinates, that particular donor will not be a candidate to supply blood to be transfused to the patient. If there is no agglutination, the donor red cell patient serum mixture is further tested for compatibility. The protocol for this further testing comprises the steps of adding albumin, incubating the mixture, washing the mixture, adding Coombs serum, centrifuging, and observing for agglutinations as previously described. If there is an agglutination, that particular donor's blood will not be suitable for transfusion to that patient. If there is no agglutination, which is confirmed by the addition of reagent check cells, that particular donor's blood will be compatible with the patient's blood and will be suitable for transfusion. That donor's unit of blood which previously had been donated to the blood bank and classified and from which the red cells used in the crossmatching tests had been obtained will be marked or identified as being suitable for transfusion to that patient. Such marking or identification may conveniently consist of applying a sticker 21 bearing the patient's accession number to the blood bag containing the donor's blood and to the other associated records maintained by the blood bank.

The donor blood will be held for a patient for a limited time because the patient, while in the hospital, may develop atypical antibodies not theretofore present in his serum. After such time, the donor's blood must be tested for compatibility against a new sample of blood from the patient.

Figure 9:
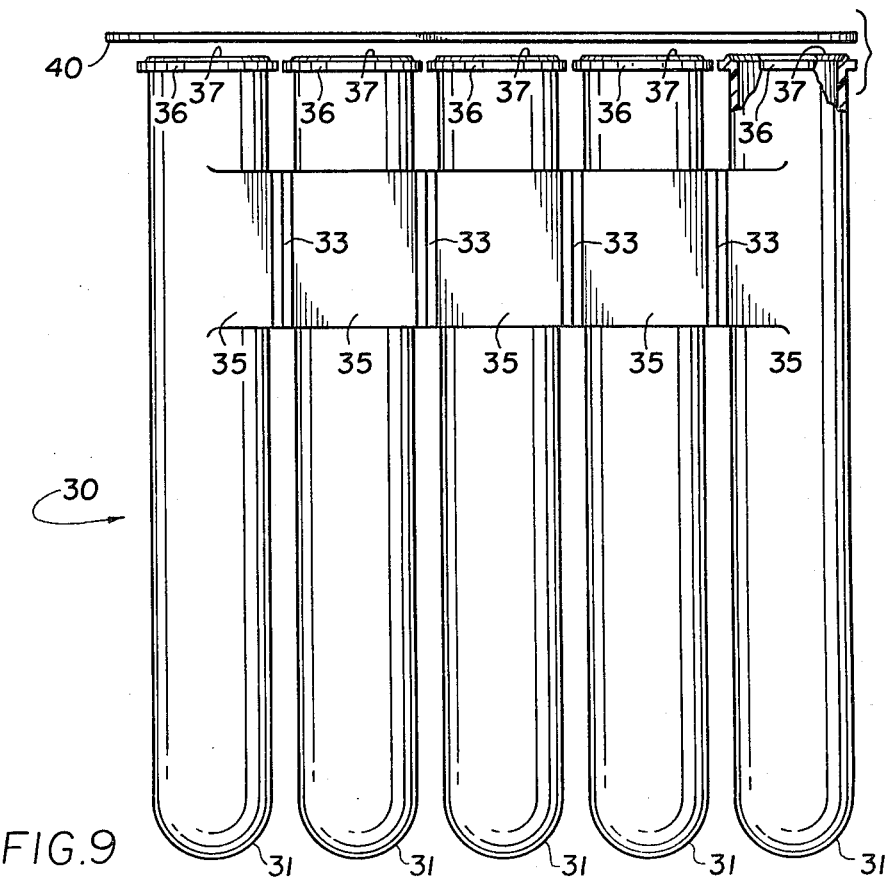
FIG. 9 is an exploded front elevational view showing a group of cuvettes adapted to be sealed with a closure means and a suitable closure tab.
Figure 10:
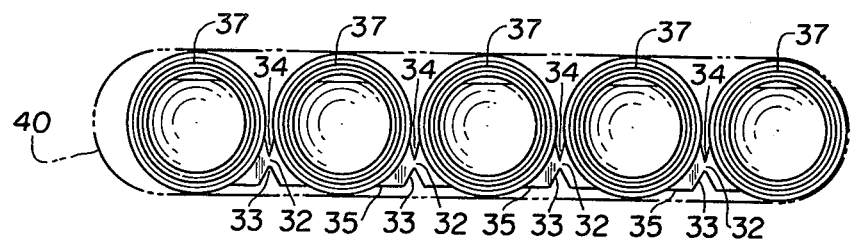
FIG. 10 is a top plan view of the cuvettes and closure tab shown in FIG. 9.

A further embodiment of the invention contemplates the provision of a pre-labeled sealed cuvette cassette that contains, in each cuvette, the reagents used for the blood tests. Since presently used reagents have a recommended shelf life of approximately six months when stored under refrigerated conditions, the provision of reagents pre-packaged directly in the test cuvettes in the volumes required for testing is a great convenience to laboratory technicians. The cassette 30 used for pre-packaged reagents is shown in FIGS. 9 and 10. Cassette 30 is seen to be similar to cassette 11 in that it comprises a plurality of cuvettes 31 joined together by connecting bridges 32 to the flat surfaces 35 of which a label, e.g., 22, is affixed. Each connecting bridge 32 is notched, as at 33 and 34, to permit the cassette to be broken between any two cuvettes 31 for the reasons described in connection with cassette 11.

The open end of each cuvette 31 is provided with a circumferential abutment 37 that has a generally triangular cross section as shown. The abutment may be formed on a rim 36 if the wall of cuvette 31 is not thick enough to accommodate the base of abutment 37. A closure tab 40 overlays the abutments 37 formed at the open ends of cuvettes 31.

Figure 11:
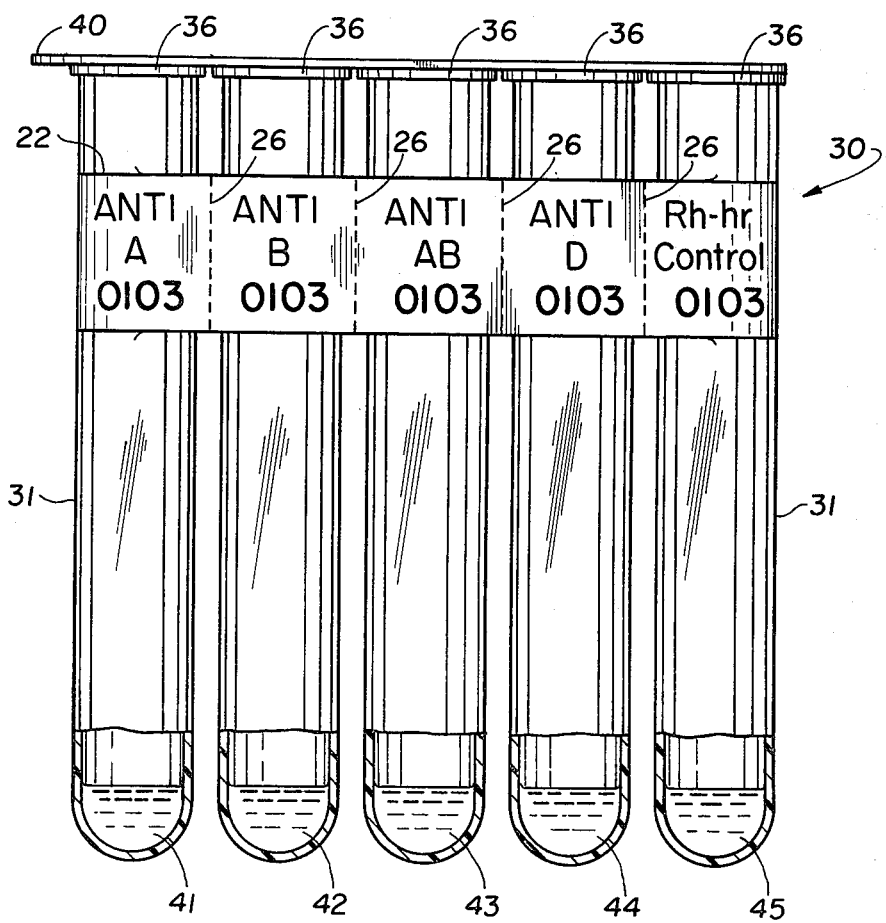
FIG. 11 is a front elevational view of a sealed group of appropriately labeled cuvettes containing reagents.

In use, for example, label 22 will be affixed to cassette 30, and anti A reagent 41 added to the cuvette 31 to which the anti A mark on label 22 is affixed. Similarly, anti B reagent 42, anti AB reagent 43, anti D reagent 44, and Rh-hr Control reagent 45 will be added to the other cuvettes of the cassette. Tab 40 will be positioned to overlay the cassette as shown in FIG. 10 and a sonic welder will be used to join the tab to cassette 30 thus sealing the reagents in their respective cuvettes. It will be noted, FIG. 11, that when tab 40 is welded to cassette 30, abutment 37 is essentially fused into the tab. Also, tab 40 is asymetrically joined to the cassette so as to provide a projecting end that enables a technician to grasp the tab and peel it from the cassette when the latter is to be used for agglutination tests. Of course, other cassettes 30 with other reagents and appropriate labels, e.g., 23 and 24, will also be provided.

It should be clear that the many cuvettes used to test a person's blood for group and antigen data, be he patient or donor, are marked with an accession number that identifies that particular person. The accession number, by means of stickers 21, is also placed on every record entry, work sheet, file card, blood bag, specimen tube, or the like, to positively associate the data, information, blood sample, etc., with the patient or donor thereby minimizing the possibility of clerical errors in recording data concerning the person's identity and blood characteristics.

Having thus described the invention, it is to be understood that many changes and variations can be made to the structure of the cassette or the structure and marking of the label without departing from the spirit and scope of the invention. For example, the flats provided on the cuvettes for the stickers could be omitted. Anti D reagents are available, e.g., Ortho Diagnostics, Inc. anti D blood grouping serum sold under the trademark "Novasera", which do not require the Rh-hr Control test. Therefore, the label or sticker marking and cuvette for that test may be eliminated. It might be preferred to do forward and reverse typing in a single cassette. Thus, a six cuvette cassette (and an appropriate label) might be used for forward and reverse typing when using an anti D reagent that does not require an Rh-hr Control test. On the other hand, if the anti D reagent requiring an Rh-hr Control test is used, a seven cuvette cassette might be preferred for forward and reverse typing in a single cassette. The order of markings on a label may be altered, or provision for more screen tests or fewer crossmatching tests may be made. Therefore, it is intended that the foregoing specification and the accompanying drawing be interpreted as illustrative rather than in a limiting sense.

What is claimed is:

1. An article of manufacture comprising a thermoplastic container for storing or holding human blood characterized in that the blood contacting surface thereof is provided with a hydrophilic coating comprising a polymer formed of a redox catalyst of sodium metabisulfite and ammonium persulfate and a monomer of 2-hydroxyethyl methacrylate that has been diluted in neat isopropanol to a solids content of approximately ¾% to 1% by weight to provide the coating solution, which polymer is non-destructive of red blood cells.

2. An article of manufacture according to claim 1 wherein the polymer is formed by adding a diluent of 95% isopropanol and 5% water on a volume basis to the monomer 2-hydroxyethyl methacrylate on a monomer to diluent weight ratio of 20:80, then adding a redox catalyst of sodium metabisulfite and ammonium persulfate having a 1:1 weight ratio to the monomer mixture in a 1:100 (redox:monomer) weight ratio, and then diluting the polymer thus formed in neat isopropanol to a solids content of approximately ¾% to 1% by weight to provide the coating solution.

3. An article of manufacture comprising a plurality of thermoplastic elongated cylindrical test-tube like cuvette means integrally formed into a linear group of individual cuvette means with adjacent cuvette means connected together by a frangible member, each frangible member being a single element breakable along a line parallel to the longitudinal axis of a cuvette means, wherein each cuvette means is provided adjacent its upper end with a flat surface substantially tangent to the outer surface of said cuvette means and having a width approximately equal to the diameter of the cuvette means, the flat surface of each cuvette means forming a co-planar array of spaced apart flat surfaces adapted to receive a single label bearing blocks of data separated by perforation means such that each perforation means will align with a space between said flat surfaces and each block of data can be secured to the flat surface of an individual cuvette means, and wherein the interior surface of each cuvette means comprises a hydrophilic polymer coating formed of a redox catalyst of sodium metabisulfite and ammonium persulfate and a monomer of 2-hydroxyethyl methacrylate that has been diluted in neat isopropanol to a solids content of approximately ¾% to 1% by weight to provide the coating solution, which polymer does not lyse red blood cells nor potentiate false antigen antibody reactions.

4. An article of manufacture according to claim 3 wherein the polymer is formed by adding a diluent of 95% isopropanol and 5% water on a volume basis to the monomer 2-hydroxyethyl methacrylate on a monomer to diluent weight ratio of 20:80, then adding a redox catalyst of sodium metabisulfite and ammonium persulfate having a 1:1 weight ratio to the monomer mixture in a 1:100 (redox:monomer) weight ratio, and then diluting the polymer thus formed in neat isopropanol to a solids content of approximately ¾% to 1% by weight to provide the coating solution.

5. An article of manufacture according to claim 3 including label means adapted for attachment to said plurality of cuvette means, said label means containing blocks of data each containing different reagent information and a common patient identification indicia so that, when said label means is attached to said plurality of cuvette means, a block of data aligned with a cuvette means includes information as to the reagent used in that cuvette means for a blood bank test and the patient identification indicia.

6. An article of manufacture according to claim 5 wherein said label means is provided with transverse rows of perforations separating each block of data from the adjacent block of data, said rows of perforations being spaced from each other so as to be in alignment with the lines along which the frangible members connecting individual cuvette means break when the label means is attached to the plurality of cuvette means so that when said cuvette means are separated into individual or a sub-group cuvette means said label means will tear along the row of perforations aligned with the broken frangible member.

7. An article of manufacture according to claim 5 including a plurality of different test reagents, one in each of said cuvette means, the reagent in a cuvette means conforming to the reagent information on the part of the label means aligned with that cuvette means, and separate sealing means closing each cuvette means.

* * * * *